United States Patent
Fukui et al.

[11] Patent Number: 6,114,279
[45] Date of Patent: Sep. 5, 2000

[54] CATALYST FOR METHANOL SYNTHESIS AND REFORMING

[75] Inventors: Hideo Fukui, Toyama; Masayuki Kobayashi, Miyagi; Tadashi Yamaguchi, Sendai; Hironori Arakawa, Tsukuba; Kiyomi Okabe, Tsukuba; Kazuhiro Sayama, Tsukuba; Hitoshi Kusama, Tsukuba, all of Japan

[73] Assignees: Director-General of Agency of Industrial Science and Technology; YKK Corporation, both of Tokyo, Japan

[21] Appl. No.: 09/050,207

[22] Filed: Mar. 30, 1998

[30] Foreign Application Priority Data

Mar. 31, 1997 [JP] Japan .................................. 9-080936
Jun. 30, 1997 [JP] Japan .................................. 9-187237

[51] Int. Cl.$^7$ .................................................. B01J 23/02
[52] U.S. Cl. .......................... 502/342; 502/326; 502/327; 502/328; 502/329; 502/330; 502/331; 502/332; 502/340; 502/341; 502/343
[58] Field of Search ................................. 502/328, 326, 502/327, 329, 330, 331, 332, 340, 341, 342, 343

[56] References Cited

U.S. PATENT DOCUMENTS

| | | | |
|---|---|---|---|
| 3,790,505 | 2/1974 | Casey et al. . | |
| 4,507,403 | 3/1985 | Asakawa | 518/713 |
| 4,535,071 | 8/1985 | Schneider et al. | 502/342 |
| 4,565,803 | 1/1986 | Schoenthal et al. | 502/303 |
| 4,588,848 | 5/1986 | Butter et al. | 568/885 |
| 4,596,782 | 6/1986 | Courty et al. | 502/302 |
| 4,598,061 | 7/1986 | Schneider et al. | 502/303 |
| 4,666,945 | 5/1987 | Osugi et al. | 518/713 |
| 4,801,574 | 1/1989 | Brown et al. | 502/342 |
| 4,808,562 | 2/1989 | Kubersky et al. | 502/172 |
| 5,128,307 | 7/1992 | Wanjek et al. | 502/342 |
| 5,155,086 | 10/1992 | Thakur et al. | 502/342 |
| 5,453,412 | 9/1995 | Deckers et al. | 502/342 |
| 5,635,439 | 6/1997 | Fukui et al. | 502/328 |

FOREIGN PATENT DOCUMENTS

| | | |
|---|---|---|
| 50-68983 | 6/1975 | Japan . |
| 55-106543 | 8/1980 | Japan . |
| 56-70836 | 6/1981 | Japan . |
| 57-7256 | 1/1982 | Japan . |
| 57-130547 | 8/1982 | Japan . |
| 59-102443 | 6/1984 | Japan . |
| 59-222232 | 12/1984 | Japan . |
| 60-147244 | 8/1985 | Japan . |
| 60-179145 | 9/1985 | Japan . |
| 60-190232 | 9/1985 | Japan . |
| 60-209255 | 10/1985 | Japan . |
| 62-53739 | 3/1987 | Japan . |
| 3-68450 | 3/1991 | Japan . |
| 4-122450 | 4/1992 | Japan . |
| 5-168936 | 7/1993 | Japan . |
| 6-170231 | 6/1994 | Japan . |
| 6-312138 | 11/1994 | Japan . |
| 8-215571 | 8/1996 | Japan . |
| 8-229399 | 9/1996 | Japan . |

*Primary Examiner*—Tom Dunn
*Assistant Examiner*—Cam N. Nguyen
*Attorney, Agent, or Firm*—Finnegan, Henderson, Farabow, Garrett & Dunner, L.L.P.

[57] ABSTRACT

A catalyst for methanol synthesis and reforming which is constituted of copper, zinc, and aluminum oxides and has a structure comprising copper or copper oxide particles covered with a film of aluminum oxide and zinc oxide. The copper or copper oxide particles preferably have a particle size of 1 to 100 nm. The film of aluminum oxide and zinc oxide preferably has a thickness of 0.1 to 100 nm. The proportions of the copper, zinc, and aluminum elements are 68.0 to 86.0% by weight, 4.5 to 21.0% by weight, and 2.0 to 20.0% by weight, respectively. The foregoing highly active catalyst comprising copper, zinc, and aluminum oxides can be obtained not by a costly special technique but by the coprecipitation method, which is the most common process for catalyst production, without using any additive element.

6 Claims, 3 Drawing Sheets

CATALYST FOR METHANOL SYNTHESIS AND REFORMING

BACKGROUND OF THE INVENTION

1. Field of the Invention

The present invention relates to a catalyst which is used for the hydrogenation of carbon dioxide or carbon monoxide in synthesizing an alcohol and/or a hydrocarbon by reacting carbon dioxide, carbon monoxide, or a carbon dioxide/carbon monoxide mixture with hydrogen gas, or which is used for steam reforming in producing hydrogen from an alcohol and water.

2. Description of the Prior Art

Investigations for the development of methanol synthesis catalysts have been made from long ago. Especially since the publication of the basic patent issued to ICI in 1968 (U.S. Pat. No. 3,790,505), catalysts constituted of copper, zinc, and aluminum oxides and produced by a coprecipitation process have been known to be highly active in methanol synthesis. Many inventions relating thereto have been made. These catalysts have been put to industrial use in plants where methanol is produced from a synthesis gas and in plants where hydrogen is produced by the steam reforming of methanol, which is the reverse reaction.

Recently, investigations are increasingly being made on the conversion of carbon dioxide to methanol with such a methanol synthesis catalyst as a measure in mitigating the problem of global warming by carbon dioxide. However, in order for carbon dioxide generated in a large quantity as in fossil-fuel combustion to be converted to methanol, it should have high convertibility sufficient to cope with extremely rapid combustion reactions. Consequently, a catalyst having even higher activity than conventional ones is earnestly desired.

For example, a reaction in the steam reforming of methanol is shown by (1).

$$CH_3OH + H_2O \rightarrow 3H_2 + CO_2 \tag{1}$$

A reaction for methanol synthesis is shown by (2).

$$3H_2 + CO_2 \rightarrow CH_3OH + H_2O \tag{2}$$

Known catalysts relating to these reactions include the following. Examples of catalysts comprising copper, zinc, and aluminum oxides and further containing at least one additive include: one containing a rare earth element or zirconium described in Japanese Patent Laid-Open No. 60-209255; one containing yttrium or lanthanide or actinide element described in Japanese Patent Laid-Open No. 60-147244; one containing chromium oxide and silver described in Japanese Patent Laid-Open No. 4-122450; one containing chromium oxide and lanthanum oxide described in Japanese Patent Laid-Open No. 5-168936; one containing gallium, vanadium, molybdenum, and tungsten described in Japanese Patent Laid-Open No. 6-312138; and one containing titanium and zirconium oxides described in Japanese Patent Laid-Open No. 8-229399. Furthermore, catalysts constituted only of three components, i.e., copper, zinc, and aluminum oxides, are described in Japanese Patent Laid-Open Nos. 50-68983, 55-106543, 56-70836, 57-130547, 57-7256, 59-222232, 59-102443, 60-190232, 60-179145, 62- 53739, 3-68450, 6-170231, etc. The Examples given in these references show that the effective ranges of the proportions in the composition of copper, zinc, and aluminum oxides are from 30 to 70% by weight as Cu, from 20 to 70% by weight as Zn, and up to 15% by weight as Al, respectively.

Industrial catalysts actually used in plants for methanol synthesis and steam reforming of methanol were examined for composition and structure. As a result, these catalysts were found to have a composition in that range and have a structure comprising aluminum oxide on the order of micrometer and, coexistent therewith, copper oxide and zinc oxide on the order of tens of nanometers. Since these three components in the structure were not always effectively in contact with each other, the structure was unable to realize high activity. Therefore, for obtaining even higher catalytic activity, there has been room for improvement in catalyst structure with respect to the configuration of particles.

Among the prior art catalysts described above, those obtained by adding additives, i.e., titanium, zirconium, gallium, palladium, vanadium, molybdenum, tungsten, yttrium, lanthanide and/or actinide elements, to copper, zinc, and aluminum oxides are unsuitable for industrial use, because these additive elements are far more expensive than copper, zinc, and aluminum.

In contrast, the catalysts constituted only of copper, zinc, and aluminum oxides are satisfactory in cost. However, these catalysts in which the proportions of copper, zinc, and aluminum are in the ranges of 30 to 70% by weight, 20 to 70% by weight, and up to 15% by weight, respectively, cannot have high activity when produced by ordinary processes, e.g., the coprecipitation method. Based on data on the properties of catalysts produced by us by the coprecipitation method so as to have compositions within the above range, it is presumed that the activity of even the catalysts having the most effective composition is, at the most, about two times that of the industrial catalysts which consist of copper, zinc, and aluminum oxides and are currently used for methanol synthesis. It is therefore thought that a catalyst having a composition within the above range and having even higher performance cannot be realized unless a special production process such as that disclosed, e.g., in Japanese Patent Laid-Open No. 8-215571 is used.

SUMMARY OF THE INVENTION

An object of the present invention is to provide a highly active catalyst for methanol synthesis and reforming, comprising copper, zinc, and aluminum oxides not by a costly special technique but by the coprecipitation method, which is said to be the most common catalyst production process, without using any harmful or expensive additive element.

In view of the problems described above, the present inventors made close investigations on the optimum conditions for achieving a high activity from the angles of the composition and the particle structure of catalysts which are constituted of copper, zinc, and aluminum oxides and have been produced, for example, by the known coprecipitation method comprising adding an alkaline solution containing an alkali carbonate, alkali hydrogencarbonate, alkali hydroxide, ammonia, or the like to a known aqueous solution of a mixture of copper nitrate, zinc nitrate, and aluminum nitrate, reacting the resultant mixture to obtain a precipitate, washing the precipitate, recovering the same by filtration, and then baking it. As a result, the present inventors found a specific catalyst structure in which the three components of copper oxide, zinc oxide and aluminum oxide most effectively interact with one another and an optimal composition which exhibits specifically high activity. The present invention has been completed based on this finding. More specifically, the present invention is directed to a catalyst for methanol synthesis and reforming which is constituted of copper, zinc, and aluminum oxides and has a structure comprising copper or copper oxide particles covered with a film of aluminum oxide and zinc oxide.

DETAILED DESCRIPTION OF THE PREFERRED EMBODIMENTS

Figure 1:
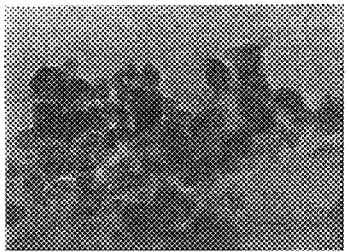
FIG. 1 shows transmission electron photomicrographs used for evaluating the structures of the catalysts described in the Examples and the Comparative Example, and further shows a model illustration of the photographs.

In order for the catalyst of the present invention constituted of copper, zinc, and aluminum oxides to have the high activity, it should have a structure in which copper or copper oxide particles are covered with a film of aluminum oxide and zinc oxide. This structure is characterized in that the particles constituted of copper or an oxide thereof have a particle size of 1 to 100 nm, preferably 1 to 50 nm, and that the coating film of zinc and aluminum oxides has a thickness of 0.1 nm (a monoatomic film) to 100 nm, preferably 0.1 to 50 nm. The reason why the copper or copper oxide particles are regulated so as to have a size of 1 to 100 nm is that copper is an active element and hence it is important to reduce the particle size as much as possible so as to maintain a large surface area as a whole. However, excessive reduction in particle size impairs the thermal stability of the particles because of the heightened surface energy, so that the particles are susceptible to sintering. Therefore, the optimal range of the size of the particles is from 1 to 100 nm from the standpoint of a balance between activity and thermal stability. The reason why the thickness of the coating film of zinc and aluminum oxides is regulated to 0.1 to 100 nm is that the catalytically effective sites are present only around the interfaces between the copper or copper oxide and the layer of zinc and aluminum oxides. Namely, too thick a coating film does not contribute to an improvement of activity since no increase in the proportion of the interfaces results.

The proportions of the copper, aluminum, and zinc elements are 68.0 to 86.0% by weight, 2.0 to 20.0% by weight, and 4.5 to 21.0% by weight, respectively, and are preferably 68.0 to 84.0% by weight, 4.0 to 17.0% by weight, and 5.0 to 21.0% by weight, respectively.

When the catalyst has copper, aluminum, and zinc proportions especially in the ranges of 72.0 to 82.0% by weight, 6.0 to 15.0% by weight, and 7.7 to 18.0% by weight, respectively, it has an activity at least 3 times that of commercial industrial catalysts constituted of copper, zinc, and aluminum oxides. In particular, when the catalyst has copper, aluminum, and zinc proportions in the ranges of 74.0 to 81.0% by weight, 6.6 to 13.0% by weight, and 10.0 to 14.0% by weight, respectively, it has an activity at least 3.5 times that of the commercial catalysts.

The reasons why the proportion of copper is regulated to 68.0 to 86.0% by weight are as follows. Since copper serves as the active element in the intended reactions, no high activity can be obtained if the proportion thereof is lower than 68.0% by weight. If the proportion of copper exceeds 86.0% by weight, the dispersibility of copper is impaired due to sintering and this results in not only reduced activity but also significantly reduced durability. Aluminum interacts with copper and zinc to function not only to enhance the activity but also to highly disperse the copper stably. Consequently, if the proportion of aluminum is lower than 2.0% by weight, the dispersibility of copper is impaired, resulting in reduced activity and significantly reduced durability. On the other hand, if the proportion of aluminum exceeds 20.0% by weight, the interaction between the aluminum and the copper or zinc is unbalanced, resulting in significantly reduced activity. Zinc functions to control the oxidized state of the copper present on the catalyst surface, and this control considerably influences catalytic activity. When the proportions of copper and aluminum are in the respective ranges specified above and zinc is present in an amount of 4.5 to 21.0% by weight, then the zinc functions to enable the catalyst to have significantly elevated activity. On the other hand, if the proportion of zinc is outside the above range, the balanced oxidized state of copper is impaired and no high activity can be obtained.

For these reasons, a catalyst structure is employed which comprises copper or copper oxide particles covered with a film of aluminum oxide and zinc oxide, and in which the amounts of these components are in the respective ranges shown above. As a result, a catalyst having durability comparable to that of the industrial catalysts and having extremely high activity is obtained by the easy precipitation method (wet process or liquid-phase process).

The present invention will now be described by reference to Examples and Comparative Examples.

EXAMPLES 1 to 20

Given amounts of copper nitrate trihydrate, zinc nitrate hexahydrate, and aluminum nitrate nonahydrate were dissolved in 1 liter of ion-exchanged water to obtain solution a, while 53 g of sodium carbonate was dissolved in 1 liter of ion-exchanged water to obtain solution b. Solution b was dropped into solution a under stirring with a stirrer to form a precipitate. The precipitate was repeatedly washed in order to remove sodium ions contained therein. This precipitate was recovered by filtration, dried at 80° C. for 12 hours, and then baked at 300° C. for 1 hour. Thus, catalysts each having a composition within the range shown in the claims (Examples 1 to 20) were obtained. These catalysts were examined for catalytic performance in the catalytic hydrogenation of carbon dioxide into methanol as follows. An $H_2/CO_2$ mixed gas ($H_2:CO_2=3:1$) was passed through a fixed-bed pressure reactor under the conditions of a reaction temperature of 250° C. and a reaction pressure of 5 MPa. The reaction product was analyzed with an on-line gas chromatograph. In Table 1 are shown the results of the compositional analysis of the catalysts obtained and the catalytic performances of the catalysts [space time yield of methanol: the amount of methanol yielded (g) per unit time (hour) per unit catalyst weight (kg)] determined in various proportions of the $H_2/CO_2$ mixed gas to the catalyst [W/F; W is the weight of the catalyst (g) and F is the flow rate of the mixed gas (mol/h)] so as to show a carbon dioxide conversion of 10%.

In the Table, the catalysts satisfying the compositional and structural requirements according to the present invention are indicated by ○ and those not satisfying the same are indicated by x.

EXAMPLE 21

A 0.5 N sodium hydroxide solution (0.5 liter) was dropped into a solution obtained by dissolving 5.8 g of copper nitrate trihydrate in 0.5 liter of ion-exchanged water, while heating the copper nitrate solution at 80° C. under stirring with a stirrer. Thus, precipitate a was obtained. Separately 0.5 liter of a 0.5 N sodium carbonate solution was dropped into a solution obtained by dissolving 3.53 g of aluminum nitrate nonahydrate in 0.5 liter of ion-exchanged water, while stirring the aluminum nitrate solution with a stirrer. Thus, precipitate b was obtained. Precipitates A and B each was sufficiently washed with water until sodium ions did not come to be detected. Thereafter, the precipitates dispersed in ion-exchanged water were mixed. In this mixture was dissolved 1.00 g of zinc nitrate hexahydrate. Thereinto was then dropped 0.5 liter of a 0.5 N sodium carbonate solution under stirring with a stirrer to form a precipitate. The precipitate was repeatedly washed in order to remove sodium ions contained therein. This precipitate was recovered by filtration, dried at 80° C. for 12 hours, and then baked at 300° C. for 1 hour to obtain a catalyst. The catalytic performance thereof was evaluated in the same manner as in Examples 1 to 20. The results of the compositional analysis of the catalyst obtained and the catalytic performance thereof are shown in Table 1.

COMPARATIVE EXAMPLES 1 to 13

Catalysts each having a composition outside the ranges shown in the claims (Comparative Examples 1 to 13) were obtained using copper nitrate trihydrate, zinc nitrate hexahydrate, aluminum nitrate nonahydrate, and sodium carbonate in the same manner as in Examples 1 to 20. The catalytic performances thereof were evaluated in the same manner as in Examples 1 to 20. The results of the compositional analysis of the catalysts obtained and the catalytic performances thereof are shown in Table 1.

COMPARATIVE EXAMPLE 14

Three solutions were obtained by separately dissolving 5.80 g of copper nitrate trihydrate, 3.53 g of aluminum nitrate nonahydrate, and 1.00 g of zinc nitrate hexahydrate in 0.5 liter of ion-exchanged water. Into each of the three solutions was dropped, under stirring with a stirrer, 0.5 liter of a 0.5 N sodium carbonate solution to cause precipitation. The three precipitates each was sufficiently washed with water until sodium ions did not come to be detected. The precipitates washed were recovered by filtration. These wet precipitates were added to the same ion-exchanged water and mixed together by stirring. Thereafter, the mixture was recovered by filtration, dried at 80° C. for 12 hours, and then baked at 300° C. for 1 hour to obtain a catalyst. The catalytic performance thereof was evaluated in the same manner as in Examples 1 to 20. The results of the compositional analysis of the catalyst obtained and the catalytic performance thereof are shown in Table 1.

COMPARATIVE EXAMPLE 15

Three solutions were obtained by separately dissolving 6.16 g of copper nitrate trihydrate, 1.86 g of aluminum nitrate nonahydrate, and 1.12 g of zinc nitrate hexahydrate in 0.5 liter of ion-exchanged water. Into each of the three solutions was dropped, under stirring with a stirrer, 0.5 liter of a 0.5 N sodium carbonate solution to cause precipitation. The three precipitates each was sufficiently washed with water until sodium ions did not come to be detected. The precipitates washed were recovered by filtration. These wet precipitates were added to the same ion-exchanged water and mixed together by stirring. Thereafter, the mixture was recovered by filtration, dried at 80° C. for 12 hours, and then baked at 300° C. for 1 hour to obtain a catalyst. The catalytic performance thereof was evaluated in the same manner as in Examples 1 to 20. The results of the compositional analysis of the catalyst obtained and the catalytic performance thereof are shown in Table 1.

TABLE 1

| Catalyst | Weight of material used (g) | | | Catalyst composition (wt %) | | | Space time yield of methanol (g/kg·h) | W/F (g·h/mol) | Invention | |
|---|---|---|---|---|---|---|---|---|---|---|
| | Copper nitrate trihydrate | zinc nitrate hexahydrate | Aluminun nitrate nonahydrate | Cu | Zn | Al | | | structure | composition |
| Example 1 | 5.17 | 1.87 | 3.20 | 68.0 | 20.5 | 11.5 | 1204 | 2.1 | ○ | ○ |
| Example 2 | 5.40 | 1.59 | 3.20 | 71.0 | 17.5 | 11.5 | 1247 | 2.1 | ○ | ○ |
| Example 3 | 5.40 | 1.87 | 2.36 | 71.0 | 20.5 | 8.5 | 1161 | 2.2 | ○ | ○ |
| Example 4 | 5.57 | 1.36 | 3.31 | 73.2 | 14.9 | 11.9 | 1376 | 1.9 | ○ | ○ |
| Example 5 | 5.59 | 1.60 | 2.49 | 73.5 | 17.5 | 9.0 | 1290 | 2.0 | ○ | ○ |
| Example 6 | 5.62 | 0.94 | 4.39 | 73.9 | 10.3 | 15.8 | 1204 | 2.1 | ○ | ○ |
| Example 7 | 5.70 | 1.09 | 3.61 | 75.0 | 12.0 | 13.0 | 1462 | 1.8 | ○ | ○ |
| Example 8 | 5.70 | 1.59 | 2.09 | 75.0 | 17.5 | 7.5 | 1290 | 2.0 | ○ | ○ |
| Example 9 | 5.80 | 1.00 | 3.53 | 76.3 | 11.0 | 12.7 | 1548 | 1.7 | ○ | ○ |
| Example 10 | 5.82 | 1.18 | 2.89 | 76.6 | 13.0 | 10.4 | 1548 | 1.7 | ○ | ○ |
| Example 11 | 5.86 | 1.46 | 1.95 | 77.0 | 16.0 | 7.0 | 1333 | 1.9 | ○ | ○ |
| Example 12 | 5.93 | 1.23 | 2.36 | 78.0 | 13.5 | 8.5 | 1505 | 1.7 | ○ | ○ |
| Example 13 | 5.97 | 0.91 | 3.20 | 78.5 | 10.0 | 11.5 | 1548 | 1.7 | ○ | ○ |
| Example 14 | 6.01 | 0.73 | 3.61 | 79.0 | 8.0 | 13.0 | 1333 | 1.9 | ○ | ○ |
| Example 15 | 6.01 | 1.32 | 1.81 | 79.0 | 14.5 | 6.5 | 1290 | 2.0 | ○ | ○ |
| Example 16 | 6.05 | 1.00 | 2.64 | 79.5 | 11.0 | 9.5 | 1505 | 1.7 | ○ | ○ |
| Example 17 | 6.16 | 0.71 | 3.11 | 81.0 | 7.8 | 11.2 | 1290 | 2.0 | ○ | ○ |
| Example 18 | 6.16 | 1.00 | 2.22 | 81.0 | 11.0 | 8.0 | 1333 | 1.9 | ○ | ○ |
| Example 19 | 6.16 | 1.12 | 1.86 | 81.0 | 12.3 | 6.7 | 1419 | 1.8 | ○ | ○ |
| Example 20 | 6.24 | 0.82 | 2.50 | 82.0 | 9.0 | 9.0 | 1247 | 2.1 | ○ | ○ |
| Example 21 | 5.80 | 1.00 | 3.53 | 76.2 | 10.7 | 12.7 | 1763 | 1.5 | ○ | ○ |

TABLE 1-continued

| Catalyst | Weight of material used (g) | | | Catalyst composition (wt %) | | | Space time yield of methanol (g/kgh) | W/F (gh/mol) | Invention | |
|---|---|---|---|---|---|---|---|---|---|---|
| | Copper nitrate tri-hydrate | zinc nitrate hexa-hydrate | Aluminun nitrate nona-hydrate | Cu | Zn | Al | | | struc-ture | compo-sition |
| Comparative Example 1 | 3.00 | 2.69 | 8.62 | 39.4 | 29.6 | 31.0 | 232 | 11.1 | ○ | x |
| Comparative Example 2 | 3.27 | 4.10 | 3.34 | 43.0 | 45.0 | 12.0 | 430 | 6.0 | ○ | x |
| Comparative Example 3 | 3.83 | 4.51 | 0.00 | 50.4 | 49.6 | 0.0 | 254 | 10.2 | ○ | x |
| Comparative Example 4 | 4.19 | 3.08 | 3.09 | 55.1 | 33.8 | 11.1 | 568 | 4.5 | ○ | x |
| Comparative Example 5 | 4.22 | 1.71 | 7.15 | 55.5 | 18.8 | 25.7 | 146 | 17.6 | ○ | x |
| Comparative Example 6 | 4.46 | 2.55 | 3.70 | 58.7 | 28.0 | 13.3 | 692 | 3.7 | ○ | x |
| Comparative Example 7 | 4.99 | 1.32 | 5.53 | 65.6 | 14.5 | 19.9 | 150 | 17.1 | ○ | x |
| Comparative Example 8 | 5.32 | 0.73 | 6.12 | 70.0 | 8.0 | 22.0 | 172 | 15.0 | ○ | x |
| Comparative Example 9 | 5.36 | 2.68 | 0.00 | 70.5 | 29.5 | 0.0 | 39 | 66.7 | ○ | x |
| Comparative Example 10 | 6.08 | 0.18 | 5.01 | 80.0 | 2.0 | 18.0 | 129 | 20.0 | ○ | x |
| Comparative Example 11 | 6.08 | 1.73 | 0.28 | 80.0 | 19.0 | 1.0 | 95 | 27.3 | ○ | x |
| Comparative Example 12 | 6.62 | 0.36 | 2.50 | 87.0 | 4.0 | 9.0 | 129 | 20.0 | ○ | x |
| Comparative Example 13 | 6.83 | 0.93 | 0.00 | 89.8 | 10.2 | 0.0 | 52 | 50.0 | ○ | x |
| Comparative Example 14 | 5.80 | 1.00 | 3.53 | 76.3 | 11.0 | 12.7 | 688 | 3.8 | x | ○ |
| Comparative Example 15 | 6.16 | 1.12 | 1.86 | 81.0 | 12.3 | 6.7 | 559 | 4.6 | x | ○ |

Figure 2:
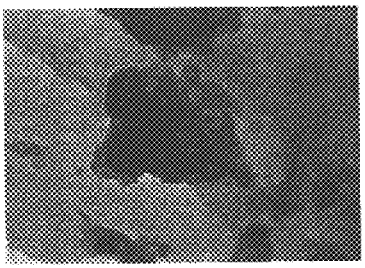
FIG. 2 shows transmission electron photomicrographs used for evaluating the structures of the catalysts described in the Comparative Examples, and further shows a model illustration of the photographs.

Transmission electron photomicrographs and model illustrations thereof used for judging the catalyst structure given in Table 1 are shown in FIGS. 1 and 2. The photographs are taken on the scale of 1 cm to 40 nm (nanometers).

Figure 3:
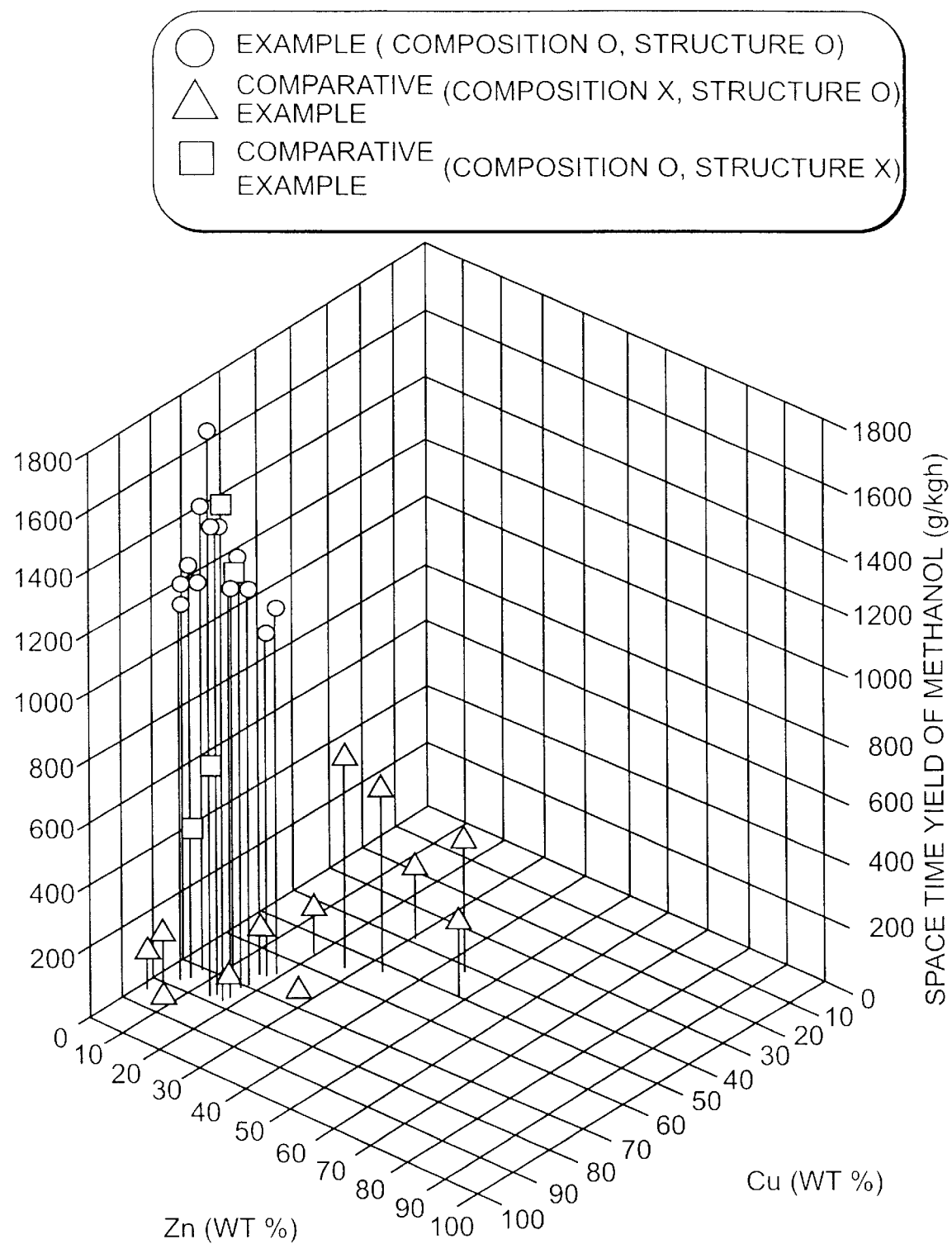
FIG. 3 shows the relationship between catalytic performance and composition in the catalysts described in the Examples and the Comparative Examples.

FIG. 3 shows the relationship between the composition (the amounts of copper and zinc in terms of % by weight, with the remainder being aluminum) and catalytic performance (space time yield of methanol) in the catalysts of the Examples and Comparative Examples shown in Table 1. In FIG. 3, ● indicates the performance of a catalyst obtained in the Example (composition, ○; structure, ○), ▲ indicates that of a catalyst obtained in the Comparative Example (composition, x; structure, ○), and ■ indicates that of a catalyst obtained in the Comparative Example (composition, ○; structure, x) {○ means that the catalyst satisfies the requirements according to the present invention, while x means that the catalyst does not satisfy the same}. The results show that the catalysts of the present invention described in the Examples can have higher activity than the conventional catalysts, because these catalysts according to the invention consist of copper, zinc, and aluminum ingredients in a proportion within the optimal range and have a structure comprising copper or copper oxide particles covered with a film of aluminum oxide and zinc oxide. These catalysts of the present invention can have an activity at least 2 times that of the industrial catalysts constituted of the same copper, zinc, and aluminum ingredients.

An extremely highly active catalyst for methanol synthesis and reforming which is usable also for the hydrogenation of carbon dioxide or carbon monoxide can be obtained according to the present invention by regulating a conventionally known catalyst constituted of copper, zinc, and aluminum oxides so as to satisfy the requirements specified above with respect to structure and composition, without using an expensive additive element or a special production technique.

What is claimed is:

1. A catalyst for methanol synthesis and reforming which is constituted of copper, zinc and aluminum oxides wherein the catalyst has a structure comprising copper or copper oxide particles covered with a film of aluminum oxide and zinc oxide, wherein the proportions of copper, zinc, and aluminum elements are 72.0 to 82.0% by weight, 7.7 to 18.0% by weight, and 6.0 to 15.0% by weight, respectively.

2. A catalyst for methanol synthesis and reforming as set forth in claim 1., wherein the copper or copper oxide particles have a particle size of 1 to 100 nm.

3. A catalyst for methanol synthesis and reforming as set forth in claim 1, wherein the film of aluminum oxide and zinc oxide with which the copper or copper oxide particles are covered has a thickness of 0.1 to 100 nm.

4. A catalyst for methanol synthesis and reforming as set forth in claim 1, wherein the proportions of the copper, zinc, and aluminum elements are 68.0 to 84.0% by weight, 5.0 to 21.0% by weight, and 4.0 to 17.0% by weight, respectively.

5. A catalyst for methanol synthesis and reforming as set forth in claim 1, wherein the proportions of the copper, zinc, and aluminum elements are 74.0 to 81.0% by weight, 10.0 to 14.0% by weight, and 6.6 to 13.0% by weight, respectively.

6. A catalyst for methanol synthesis and reforming as set forth in claim 1, which has been obtained by a precipitation process in which starting materials are present as an aqueous mixture.

* * * * *